United States Patent [19]

Klose et al.

[11] 4,418,019
[45] Nov. 29, 1983

[54] PROCESS FOR THE MANUFACTURE OF 1-AMINOALKANE-1,1-DIPHOSPHONIC ACIDS

[75] Inventors: Werner Klose, Erftstadt; Theodor Auel, Edingen, both of Fed. Rep. of Germany

[73] Assignee: Hoechst Aktiengesellschaft, Fed. Rep. of Germany

[21] Appl. No.: 327,888

[22] Filed: Dec. 7, 1981

[30] Foreign Application Priority Data

Dec. 13, 1980 [DE] Fed. Rep. of Germany ....... 3047107

[51] Int. Cl.³ ................................................ C07F 9/38
[52] U.S. Cl. .......................... 260/502.5 C; 260/465.2; 562/609; 423/317; 423/415 A
[58] Field of Search .................. 260/502.5 C, 502.4 A

[56] References Cited

U.S. PATENT DOCUMENTS

| | | | |
|---|---|---|---|
| 3,361,528 | 1/1968 | Shen | 260/502.4 A |
| 3,400,149 | 9/1968 | Quimby et al. | 260/502.4 A |
| 3,504,018 | 3/1970 | Irani et al. | 260/502.4 A |
| 3,870,750 | 3/1975 | Wollmann et al. | 260/502.5 |
| 4,060,546 | 11/1977 | Blaser et al. | 260/502.4 A |
| 4,104,366 | 8/1978 | Schmidt-Dunker et al. | 260/502.5 |
| 4,139,554 | 2/1979 | Krueger et al. | 260/502.5 |
| 4,157,364 | 6/1979 | Buckman et al. | 260/502.5 |

FOREIGN PATENT DOCUMENTS 2846835  5/1980  Fed. Rep. of Germany ... 260/502.5

OTHER PUBLICATIONS

Wagner et al., "Synthetic Organic Chemistry", 1953, p. 567.

The Merck Index, Eighth Edition, 1968, pp. 824–826.
Phosphorus and its Compounds, vol. I: Chemistry, John R. Van Wazer, pp. 281–282.

*Primary Examiner*—J. E. Evans
*Attorney, Agent, or Firm*—Connolly and Hutz

[57] ABSTRACT

The invention relates to a process for making 1-aminoalkane-1,1-diphosphonic acids of the general formula (I):

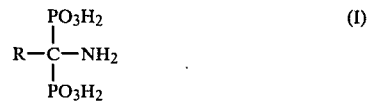

in which R stands for an aliphatic hydrocarbon radical having from 1 to 12 carbon atoms.

To this end, the invention provides:
(a) for tetraphosphorus hexoxide to be reacted with at least one compound of the general formula (II)

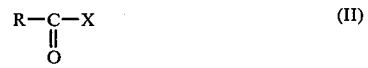

in which R has the meaning given above and X stands for an —ONH₄ or NH₂-radical, in inert gas atmosphere at elevated temperature, the molar ratio of tetraphosphorus hexoxide to the compound of general formula (II) being about 1 to 2–6; and
(b) for 1-aminoalkane-1,1-diphosphonic acid to be crystallized from the reaction mixture.

16 Claims, No Drawings

PROCESS FOR THE MANUFACTURE OF 1-AMINOALKANE-1,1-DIPHOSPHONIC ACIDS 1-aminoalkanediphosphonic acids and their derivatives are complex formers and sequestering agents which are widely used alone or in combination with further chelate formers or stabilizers in the most various fields including e.g. the treatment of water, manufacture of paper and textiles, and production of detergent and cleaning compositions.

As described in DE-PS No. 20 48 913, 1-aminoalkane-1,1-diphosphonic acids are made by reacting organic nitriles with phosphorous acid in the presence of hydrogen halides at temperatures of up to about 100° C. In this process, commercially interesting 1-aminoethane-1,1-diphosphonic acid is obtained in yields as low as about 47%, based on phosphorous acid. In addition to this, the presence of highly corrosive hydrogen halides in the process just described makes it necessary for the latter to be carried out with the use of special equipment.

A further process for making 1-aminoalkane-1,1-diphosphonic acids by reacting nitriles with phosphorous acid at elevated temperatures within the range 140° to 200° C., but in the absence of corrosive hydrogen halide has been described in DE-PS No. 26 25 767.

The commercial attractiveness of these two processes has to an increasing extent been affected by the considerably increased price of the nitriles used as feed material.

The present invention now provides a process for making 1-aminoalkane-1,1-diphosphonic acids, which permits the adverse effects of the above prior processes to be avoided (a) by processing the reaction mixture in the absence of hydrogen halides and (b) by the use of less expensive feed material than heretofore.

The present invention relates more particularly to a process for making 1-aminoalkane-1,1-diphosphonic acids of the general formula (I):

in which R stands for a straight or branched aliphatic hydrocarbon radical having from 1 to 12 carbon atoms, which comprises:

(a) reacting tetraphosphorus hexoxide with at least one compound of the general formula (II):

in which R has the meaning given above and X stands for an $-ONH_4$ or $NH_2$-radical and, if desired, with water or a compound yielding water under the reaction conditions, the reaction being effected in inert gas atmosphere and optionally in the presence of an inert diluent at elevated temperature, the molar ratio of tetraphosphorus hexoxide to the compound of general formula (II) being about 1 to 2-6, and (b) permitting 1-aminoalkane-1,1-diphosphonic acid to crystallize from the reaction mixture, if desired after distillative removal of the diluent and after cooling.

The process of this invention is particularly useful in the production of those compounds of general formula (I), in which R stands for a methyl, ethyl, 2-ethylhexyl or n-dodecyl radical.

The molar ratio of tetraphosphorus hexoxide to the other reactants is one of the parameters which critically determine the present process. In the event of tetraphosphorus hexoxide being reacted with a compound of general formula (II), in which X stands for $-ONH_4$, and water or compound yielding water, the molar ratio preferably is 1:2:2. In the event of the reaction being effected in the absence of water or compound yielding water, it is good practice to use the tetraphosphorus hexoxide and compound of general formula (II) in a molar ratio of 1:3. In this latter case, 1-aminoalkane-1,1-diphosphonic acid is obtained together with a by-product, which is a nitrile of the formula RCN, in which R has the meaning given above. This by-product can be distillatively removed from the reaction mixture, or admixed with phosphorous acid and converted to desirable diphosphonic acid.

In the event of tetraphosphorus hexoxide being reacted with the compound of general formula (II), in which X stands for $-NH_2$, water or compound yielding water, it is preferable for the reactants to be used in a molar ratio of 1:2:4. Needless to say, the molar ratio is altered in the event of the reaction being effected in the absence of water or compound yielding water, namely to 1:6. The nitrile by-product obtained in this case can also be processed as described hereinabove.

The invention also provides for the molar ratio to select for effecting the reaction to be varied in those cases in which blends of the compound of formula (II), in which X stands for $-ONH_4$ and $-NH_2$, respectively, with tetraphosphorus hexoxide are used, $(n/3+m/6)$ mols $P_4O_6$ being preferably employed for a mixture formed of n mols $RCOONH_4$ and m mols $RCONH_2$. More specifically, it is good practice, for example, to use 2 mols compound of general formula (II), in which X stands for $-ONH_4$, and 2 mols compound of general formula (II), in which X stands for $-NH_2$, per mol tetraphosphorous hexoxide. In the event of the compound of general formula (II) being employed together with water or compound yielding water, it is preferable for 1 mol compound of general formula (II), in which X stands for $-ONH_4$, for 1 mol compound of general formula (II), in which X stands for $-NH_2$, and for 3 mols water or compound yielding water to be used per mol $P_4O_6$.

The water or compound yielding water present in the batch to undergo reaction can naturally be replaced by a blend of the two components.

A preferred feature of the present invention provides for the feed materials to be reacted at a temperature of 30° to 100° C., preferably 50° to 80° C., in the presence of nitrogen or $CO_2$ as the inert gas and with the use of aliphatic or aromatic hydrocarbons with a boiling point or range of 80° to 120° C. as diluents. Useful representatives of these hydrocarbons are petroleum ether, benzene or toluene. Acetonitrile is a further useful diluent. In all those process variants in which a carboxylic acid nitrile of the formula RCN is obtained as a by-product, it is basically possible for it to be used as diluent.

A further preferred feature of the present invention finally provides for the introduction of tetraphosphorus hexoxide into the compound of general formula (II) to be completed, for the reaction mixture to be then allowed to remain over a period of about 30 to 120 minutes at reaction temperature, for the reaction temperature to be then gradually increased to 140° to 200° C. with distillative removal of the diluent, if desired, for the whole to be cooled and for 1-aminoalkane-1,1-diphosphonic acid to be crystallized from water or a suitable solvent.

The melt obtained after distillative removal of the diluent sometimes has a yellow coloration. To decolorize the product or its aqueous or alcoholic solution, it should be admixed with a minor proportion of $H_2O_2$.

The following statements are intended further to illustrate the invention.

The numerous potential variants of the process of this invention are illustrated by the following reaction equations 1 to 13:

---

1. $P_4O_6 + 2RCOONH_4 + 2H_2O \longrightarrow 2R-C(PO_3H_2)_2\cdot NH_2$

2. $P_4O_6 + 2RCOONH_4 + 2HCOOH \longrightarrow$
   $2R-C(PO_3H_2)NH_2 + CO$

3. $P_4O_6 + 3RCOONH_4 \longrightarrow 2R-C(PO_3H_2)_2NH_2 + RCN$

4. $P_4O_6 + 3RCOONH_4 + 2H_3PO_3 \longrightarrow 3R-C(PO_3H_2)_2NH_2$

5. $P_4O_6 + 2RCONH_2 + 4H_2O \longrightarrow 2R-C(PO_3H_2)_2NH_2$

6. $P_4O_6 + 2RCONH_2 + 4HCOOH \longrightarrow$
   $2R-C(PO_3H_2)_2NH_2 + 4 CO$

7. $P_4O_6 + 6RCONH_2 \longrightarrow 2R-C(PO_3H_2)_2NH_2 + 4 RCN$

8. $P_4O_6 + 6RCONH_2 + 8H_3PO_3 \longrightarrow 6R-C(PO_3H_2)_2NH_2$

9. $P_4O_6 + RCOONH_4 + RCONH_2 + 3H_2O \longrightarrow$
   $2R-C(PO_3H_2)_2NH_2$ 10. $P_4O_6 + RCOONH_4 + RCONH_2 + 3HCOOH \longrightarrow$
    $2R-C(PO_3H_2)_2NH_2 + 3 CO$ 11. $P_4O_6 + 2RCOONH_4 + 2RCONH_2 \longrightarrow$
    $2R-C(PO_3H_2)_2NH_2 + 2RCN$ 12. $P_4O_6 + 2RCOONH_4 + 2RCONH_2 + 4H_3PO_3 \longrightarrow$
    $4R-C(PO_3H_2)_2NH_2$ 13. $P_4O_6 + 2RCOONH_4 + H_2O + HCOOH \longrightarrow$
    $2R-C(PO_3H_2)_2NH_2 + CO$

---

The use of $P_4O_6$ as feed material in the process of this invention would not appear to have been obvious, for the following reasons: Tetraphosphorus hexoxide is known to undergo hydrolysis stagewise (this occurs also in the present process) via various polyphosphorous acids, among which especially those with a degree of condensation of more than 2 are thermally unstable and, in oxido-reduction reactions, decompose with formation of yellow-orange colored phosphorous suboxides, hydrogen phosphide and various phosphorus-V-acids. The decomposition, which can be demonstrated to take place at temperatures even lower than $-10°$ C., occurs even more rapidly than the hydrolysis, at temperatures higher than 50° C.

Temperatures of 50° C. and more are, however, likely to occur on subjecting tetraphosphorus hexoxide to reaction with normally solid ammonium salts of carboxylic acids or corresponding carboxylic acid amides, in view of the following: On the one hand, the reaction can reasonably be expected to be initiated only at a temperature higher than the melting point of one of the reactants; on the other hand, it might be difficult to provide for reaction heat which is evolved by a suspected strongly exothermal reaction, to be rapidly abstracted from a heterogeneous reaction mixture with a high solid matter content therein. In view of this, the artisan would scarcely suggest that tetraphosphorus hexoxide should be used as a starting material in the present process. By adding water or a compound yielding water to the material to undergo reaction, or by the use of the compounds of general formula (II) and $P_4O_6$ in molar ratios which make it possible for the $H_2O$ separable from the compound of general formula (II) to completely hydrolyze the $P_4O_6$, it is possible to inhibit those difficulties which indeed would have been expected to occur.

The present process compares favorably with the prior art in respect of the following points: Use is made therein of commercially readily accessible and inexpensive feed material, and desirable final product is obtained in yields considerably higher than those obtained in the process described in DE-PS No. 20 48 913.

EXAMPLE 1

A blend of 40.5 g (0.525 mol) ammonium acetate and 9 g (0.5 mol) water was placed in an agitator-provided vessel maintained under nitrogen atmosphere and preheated to about 26° C. by means of a heating bath. Next, 55 g (0.25 mol) molten $P_4O_6$ which had a temperature of about 26° C. and came from a heatable dropping funnel was metered within 3 hours into the agitator-provided vessel. The temperature of the reaction mixture increased immediately to more than 30° C. and ultimately to about 50° C. as the introduction of further $P_4O_6$ went on. Towards the end of the $P_4O_6$-addition, the very viscous mixture was heated from the outside to 70° C. so that it remained stirrable and, after the $P_4O_6$-addition was terminated, maintained for 1 hour at that temperature and ultimately gradually heated to 160° C. The product colorless heretofore assumed a yellow coloration. After cooling down to about 80° C., the product was taken up in 100 ml water, and the yellow liquid rendered turbid by undissolved solid matter was admixed with hydrogen peroxide (30% strength) so as to obtain a clear solution. The solution was concentrated, admixed with some isopropanol and 45 g white crystalline matter was obtained by suction filtration. It was dried. $^{31}$P-NMR-spectroscopy indicated it was 1-aminoethane-1,1-diphosphonic acid.

EXAMPLE 2

The procedure was as described in Example 1, but a blend of 40.5 g (0.525 mol) ammonium acetate and 23 g (0.5 mol) formic acid was reacted with 55 g (0.25 mol) $P_4O_6$. 45 g 1-aminoethane-1,1-diphosphonic acid was obtained.

EXAMPLE 3

48.8 g (0.63 mol) ammonium acetate was suspended in 68 g (1.66 mols) acetonitrile in a flask which was scavenged with nitrogen, provided with an agitator and had a fractionating column mounted thereon, and the suspension was heated to about 80° C. under reflux. Next, 46.4 g (0.21 mol) molten $P_4O_6$ was added dropwise to the boiling mixture, the temperature being maintained at 80°–90° C. While the temperature was gradually increased to 160° C., 85.1 g distillate containing 91.5% acetonitrile and 8.2% acetic acid, corresponding to 77.9 g (0.190 mol)acetonitrile and 7.0 g (0.24 mol) acetic acid, was removed through a short column at a head temperature of 84°–89° C. After deduction of the acetonitrile feed material, 11.9 g (0.24 mol) acetonitrile was found to have been obtained as by-product. The acetonitrile/acetic acid mixture was recycled, after conversion of the acetic acid to ammonium acetate. The colorless residue retained in the flask was boiled for a short while in an ethanol/water-mixture (4:1) and 57.1 g 1-aminoethane-1,1-diphosphonic acid was obtained in a yield of 66%.

EXAMPLE 4

83.6 g (1.416 mols) acetamide was dissolved at about 40° C. in 45.4 g (1.1 mols) acetonitrile in a flask which was provided with a stirrer and had a fractionating column mounted thereon. Next, 52 g (0.236 mol) $P_4O_6$ was added dropwise at 40°–55° C. After this had been done, the temperature of the reaction mixture was gradually increased to 163° C. while 85.4 g distillate containing 96.4% acetonitrile and 3.5% acetic acid, corresponding to 82.3 g (2.008 mols) acetonitrile and 3.0 g (0.05 mol) acetic acid, was removed at a head temperature of 81°–85° C. After deduction of the acetonitrile feed material, 36.9 g (0.908 mol) acetonitrile was found to have been formed as a by-product. The yellow residue retained in the flask was oxidized with $H_2O_2$ and boiled in an ethanol/water-mixture (4:1). 60.1 g colorless crystalline 1-aminoethane-1,1-diphosphonic acid, corresponding to a yield of 60%, was obtained.

EXAMPLE 5

29.5 g (0.5 mol) acetamide was dissolved in 18 g (1.0 mol) water and the solution was heated to 80° C. Next, 55 g (0.25 mol) molten tetraphosphorus hexoxide was added dropwise, the mixture was maintained for 30 minutes at 80° C. and then heated within 2 hours to 162° C. At that temperature, the reaction mixture solidified into a solid mass. After cooling, it was admixed with 13.4 g water and 15.4 g hydrogen peroxide and ultimately stirred into an ethanol/water-mixture (ratio by weight=7:1). The liquid was removed by suction filtration and the solid matter was dried. 82 g 1-aminoethane-1,1-diphosphonic acid, corresponding to a yield of 80%, based on $P_4O_6$, was obtained.

EXAMPLE 6

9.0 g (0.5 mol) water, 68.06 g (0.83 mol) phosphorous acid and 39.3 g (0.5 mol) 98% ammonium acetate was placed in an agitator-provided vessel maintained under nitrogen. Next, 54.97 g (0.25 mol) molten $P_4O_6$ which had a temperature of about 30° C. and came from a dropping funnel, was metered within 15 minutes into the solution, the reaction mixture being maintained at a temperature of less than 50° C. During $P_4O_6$-addition, the viscosity of the mixture was found to increase but did not adversely affect stirability. Next, 30 g (0.146 mol) 1-aminoethane-1,1-diphosphonic acid was added and the temperature of the reaction mixture was gradually increased to 165° C., which was maintained over a period of 90 minutes at 165° C.±5° C. After cooling down to 80° C. a crystal suspension was obtained. It was admixed with 100 ml distilled water and cooled down to room temperature with agitation. After suction-filtration and drying, 111.9 g white crystalline matter was obtained. Thin layer chromatography indicated it was 1-aminoethane-1,1-diphosphonic acid. After deduction of the quantity of 1-aminoethane-1,1-diphosphonic acid used as feed material, the yield was 81.9 g, corresponding to 79.9% of the theoretical, based on ammonium acetate used.

The clear filtrate was distillatively dehydrated in a vacuum rotary evaporator and 88.95 g of a viscous liquid composed of
- 94.8 weight % phosphorous acid
- 1.0 weight % phosphoric acid and
- 4.2 weight % 1-aminoethane-1,1-diphosphonic acid
was obtained. The filtrate so dehydrated could be used again in the next batch.

EXAMPLE 7

As described in Example 6, 9.0 g (0.5 mol) water, 75.7 g dehydrated filtrate (Example 6) corresponding to 71.8 g (0.83 mol) phosphorous acid and 54.97 g (0.25 mol) $P_4O_6$ were reacted in the presence of 30 g (0.146 mol) 1-aminoethane-1,1-diphosphonic acid. 115.0 g crystalline matter was obtained. Thin layer chromatography indicated it was 1-aminoethane-1,1-diphosphonic acid. After deduction of the quantity of 1-aminoethane-1,1-diphosphonic acid used, the yield was 85.0 g, corresponding to 82.9% of the theoretical, based on ammonium acetate used.

The filtrate was dehydrated as described in Example 6. The resulting viscous liquid was composed of:
- 93.2 weight % phosphorous acid
- 2.2 weight % phosphoric acid and
- 4.6 weight % 1-aminoethane-1,1-diphosphonic acid.

It was possible for it to be used again in the next batch.

We claim:

1. Process for making 1-aminoalkane-1,1-diphosphonic acids of the general formula (I)

in which R stands for a straight or branched aliphatic hydrocarbon radical having from 1 to 12 carbon atoms, which comprises:
(a) reacting tetraphosphorus hexoxide with at least one compound of the general formula (II)

in which R has the meaning given above and X stands for an $-ONH_4$ or $NH_2$-radical, the reaction being effected in inert gas atmosphere at a temperature within the range 30° to 100° C., the molar ratio of tetraphosphorus hexoxide to the compound of general formula (II) being about 1 to 2–6; and (b) crystallizing the 1-aminoalkane-1,1-diphosphonic acid formed and separating it from the reaction mixture.

2. The process as claimed in claim 1, wherein the substituent R stands for a methyl, ethyl, 2-ethylhexyl or n-dodecyl radical.

3. The process as claimed in claim 1, wherein tetraphosphorus hexoxide is reacted with the compound of general formula (II) in which X stands for $-ONH_4$, in the molar ratio of 1:3.

4. The process as claimed in claim 1, wherein tetraphosphorus hexoxide is reacted with the compound of general formula (II) in which X stands for $-NH_2$, in the molar ratio of 1:6.

5. The process as claimed in claim 1, wherein tetraphosphorus hexoxide is reacted with a blend of a compound of general formula (II), in which X stands for $-ONH_4$, and a compound of general formula (II), in which X stands for $-NH_2$, $(n/3+m/6)$ mols $P_4O_6$ being used for a mixture formed of n mols $RCOONH_4$ and m mols $RCONH_2$.

6. The process as claimed in claim 5, wherein 2 mols compound of general formula (II), in which X stands for $-ONH_4$, and 2 mols compound of general formula (II), in which X stands for $NH_2$, are used per mol tetraphosphorus hexoxide.

7. The process as claimed in claim 1, wherein the inert gas is selected from nitrogen or $CO_2$.

8. The process as claimed in claim 1, wherein water or a blend of water and a compound splitting off water under the reaction conditions is added to the reactant compounds, said compound splitting off water being selected from HCOOH, $RCONH_2$, and $RCOONH_4$, where R has meaning given in claim 1.

9. The process as claimed in claim 8, wherein tetraphosphorus hexoxide is reacted with the compound of general formula (II) in which X stands for $-ONH_4$, and water or a said compound splitting off water under the reaction conditions, in a molar ratio of 1:2:2.

10. The process as claimed in claim 8, wherein tetraphosphorus hexoxide is reacted with the compound of general formula (II) in which X stands for $-NH_2$, and water or a said compound splitting off water under the reaction conditions, in a molar ratio of 1:2:4.

11. The process as claimed in claim 8, wherein 1 mol of the compund of general formula (II), in which X stands for $-ONH_4$, and 1 mol of the compound of general formula (II) in which X stands for $-NH_2$, and 3 mols of water or a said compound splitting off water under the reaction conditions are used per mol tetraphosphorus hexoxide.

12. The process as claimed in claim 1, wherein the reaction is effected at a temperature within the range 50° to 80° C.

13. The process as claimed in claim 1, wherein the reaction is effected in the presence of a diluent selected from aliphatic and aromatic hydrocarbons with a boiling point or range of 80° to 120° C. and acetonitrile.

14. The process as claimed in claim 13, wherein the diluent is selected from petroleum ether, benzene, and toluene.

15. The process as claimed in claim 1, wherein the solution of the melt-like distillation residue is decolorized by means of $H_2O_2$ which is added thereto.

16. The process as claimed in claim 1, wherein, after complete introduction of tetraphosphorus hexoxide into the compound of general formula (II), the reaction mixture is allowed to remain over a period of about 30 to 120 minutes at reaction temperature, which is then gradually increased to 140°–200° C., the whole is cooled and the 1-aminoalkane-1,1-diphosphonic acid is crystallized out from water or a suitable solvent.

* * * * *